United States Patent [19]
Lingenhöle

[11] Patent Number: 5,368,479
[45] Date of Patent: Nov. 29, 1994

[54] DENTAL INSTRUMENT WITH AN ILLUMINATION DEVICE

[75] Inventor: Bernhard Lingenhöle, Mittelbiberach, Germany

[73] Assignee: Kaltenbach & Voigt GmbH & Co., Biberach/Riss, Germany

[21] Appl. No.: 63,299

[22] Filed: May 19, 1993

[30] Foreign Application Priority Data

May 21, 1992 [DE] Germany ............... 4216873

[51] Int. Cl.⁵ .............. A61C 1/00; A61C 3/00; A61C 1/08
[52] U.S. Cl. .............................. 433/29; 433/117
[58] Field of Search .................. 433/29, 126, 117

[56] References Cited

U.S. PATENT DOCUMENTS

| | | | |
|---|---|---|---|
| 3,609,641 | 9/1971 | Luce et al. | 339/93 |
| 3,671,923 | 6/1972 | Rieth | 339/93 L |
| 3,955,872 | 5/1976 | Brudy | 339/93 L |
| 4,070,567 | 1/1978 | Crompton | 362/390 |
| 4,176,263 | 11/1979 | Rousseau | 200/60 |
| 4,375,964 | 3/1983 | Knopp et al. | 433/29 |
| 4,398,885 | 8/1983 | Loge et al. | 433/126 |
| 4,514,169 | 4/1985 | Strohmaier | 433/29 |
| 4,518,355 | 5/1985 | Hoffmeister et al. | 433/29 |
| 4,655,709 | 4/1987 | Fleer | 433/29 |
| 4,938,692 | 7/1990 | Castellini | 433/29 |
| 4,967,328 | 10/1990 | Tatavoosian | 362/267 |
| 5,057,015 | 10/1991 | Fleer | 433/126 |

FOREIGN PATENT DOCUMENTS

| | | |
|---|---|---|
| 0015659 | 5/1983 | European Pat. Off. . |
| 0173159 | 8/1985 | European Pat. Off. . |
| 0238778 | 10/1986 | European Pat. Off. . |
| 0280662 | 8/1988 | European Pat. Off. . |
| 2377083 | 1/1977 | France . |
| 3513448 | 10/1986 | Germany . |
| 3104239 | 11/1986 | Germany . |
| 3332628 | 11/1988 | Germany . |

Primary Examiner—Gene Mancene
Assistant Examiner—Cindy A. Cherichetti
Attorney, Agent, or Firm—Fitzpatrick, Cella, Harper & Scinto

[57] ABSTRACT

In a medical or dental instrument having a driven treatment tool and an illumination device with a lamp, in particular for the treatment area, wherein the lamp is mounted in a plug-in socket, the plug-in socket is formed by two spring elements biassed towards one another between which the lamp is mounted to swing freely. Alternatively at least one damping element can be arranged between the holder and the lamp or the holder can be mounted elastically on the base part.

11 Claims, 3 Drawing Sheets

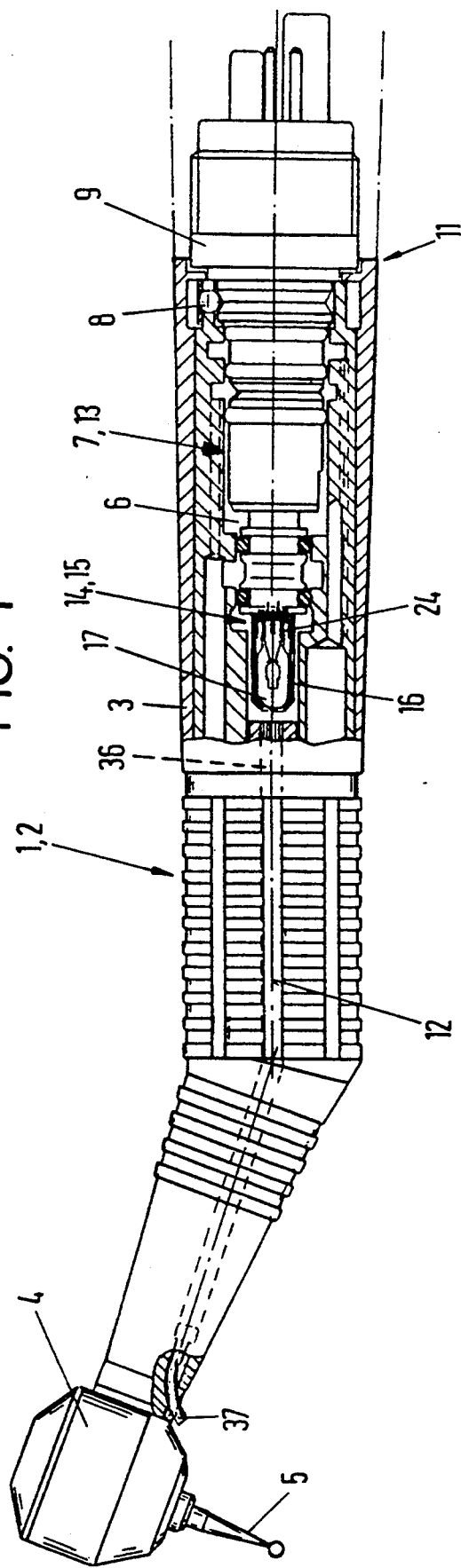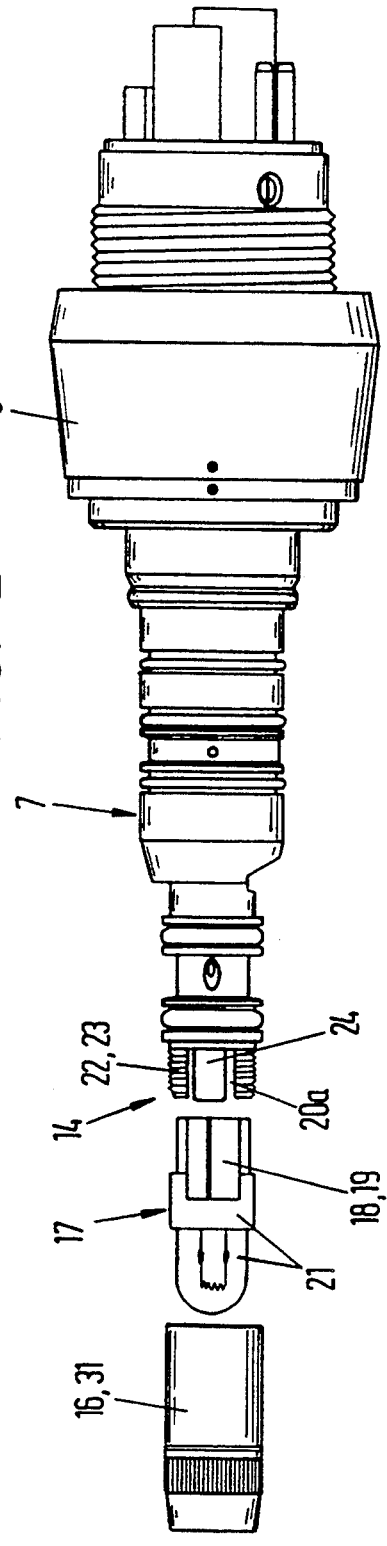

DENTAL INSTRUMENT WITH AN ILLUMINATION DEVICE

TECHNICAL FIELD OF THE INVENTION

The invention relates to a medical, for example a dental, instrument with a motor-driven treatment tool and with an illumination device.

BACKGROUND OF THE INVENTION AND PRIOR ART

With instruments of this kind it is known to generate the light necessary for illuminating the treatment area by means of an electric lamp arranged in the instrument. The lamp may be arranged in the front region of the instrument so that its light is aimed directly on to the treatment area. In particular in the case of such instruments which are in two parts, so that it is possible to exchange different treatment tools and for the purpose of disinfection, wherein the front instrument part can be connected by a quick-fitting coupling to the rear instrument part and, in particular with regard to the latter, is held rotatably thereon, it is known to arrange the lamp in the region of the rear instrument part, preferably directly behind the separating point. The light generated by the lamp is guided by means of a light conductor extending longitudinally in the front instrument part to a light emission opening which is located in the front region of the front instrument part and is aimed towards the treatment area. The lamp may be arranged in the axis of rotation or the longitudinal centre axis of the instrument, as described in DE 31 04 239 C2, or the lamp may be arranged eccentrically, as described in DE 33 32 628 C2.

Owing to the motor drive for the treatment tool, which may be either a mechanical drive (DE 33 32 628 C2) or a turbine drive (DE 31 04 239 C2), vibrations are generated in the instrument which also act on the lamp. In the known constructions, in which the lamp is held immovably in the region of its plug-in foot and/or its lamp bulb, vibrations lead to premature failure of the lamp. With lamps having a spiral-wound filament the most common cause of failure is a break in the spiral-wound filament.

An instrument of the kind described in the introduction is in public use. In this known construction the lamp holder has a plug-in socket in the form of a hollow cylindrical bush, into which the lamp foot can be inserted, there being in the bush two contact elements which are spaced apart and formed by thoroughly bendable spring arms between which the lamp foot can be inserted. Owing to the fixed seating in the bush, the lamp is mounted rigidly. The contact elements serve only for electrical contacting. Furthermore the contact elements are supported laterally on a holding ring, with the intermediate arrangement of an insulating layer. In the contact position the contact elements are therefore practically immovable.

OBJECT OF THE INVENTION

It is an object of the invention to prolong the service life of the lamp in an instrument of the kind mentioned in the introduction.

SUMMARY OF THE INVENTION

According to the present invention there is provided a medical or dental instrument having a driven treatment tool and an illumination device with a lamp, in particular for the treatment area, wherein the lamp is mounted in a plug-in socket, and wherein the plug-in socket is formed by two spring elements biassed towards one another between which the lamp is mounted to swing freely.

According to the present invention there is also provided a medical or dental instrument having a driven treatment tool and an illumination device with a lamp, in particular for the treatment area, wherein the lamp is mounted in a holder, and wherein at least one damping element is arranged between the holder and the lamp.

According to the present invention there is further provided a medical or dental instrument having a driven treatment tool and an illumination device with a lamp, in particular for the treatment area, wherein the lamp is mounted in a holder that is carried by a base part, and wherein the holder is mounted elastically on the base part.

With the instrument according to the invention the lamp is mounted to float or is mounted elastically resiliently in the region of its lamp foot and/or its bulb. As a result of this mounting a large percentage of the vibrations are absorbed in a damped manner in the mount so that only a very reduced amount of vibrations can be conveyed to the lamp and the service life of the lamp is increased substantially.

As a result of the floating or elastically resilient mounting of the lamp, the lamp follows the vibrations from a centre position at a reduced and/or delayed extent so that the amplitude of the vibrations, and speed of vibration, effective at the lamp are reduced.

To achieve the advantage according to the invention it is not absolutely necessary that the lamp has an overall floating, elastically resilient or free swinging mount. It suffices to mount the lamp in its front and/or rear region in the manner described above. By this means the influence of the vibrations on the lamp are substantially reduced.

Features are set forth in relation to embodiments of the invention which offer further advantages: enable rapid and simple mounting and dismantling and simple and economical manufacture, improve electrical contacting whilst ensuring a compact construction.

BRIEF DESCRIPTION OF THE DRAWINGS

The invention and further advantages attainable thereby will now be described in more detail with reference to preferred exemplary embodiments shown in the drawings, in which:

FIG. 1 shows a front instrument part of a dental treatment instrument and a coupling pin of a quick-fit coupling for the front instrument projecting from the rear instrument;

FIG. 2 shows, in an enlarged representation, the coupling pin of the quick-fit coupling as a lamp carrier, wherein the lamp is withdrawn from its socket;

DETAILED DESCRIPTION OF PREFERRED EMBODIMENTS ACCORDING TO THE INVENTION

Figure 3:
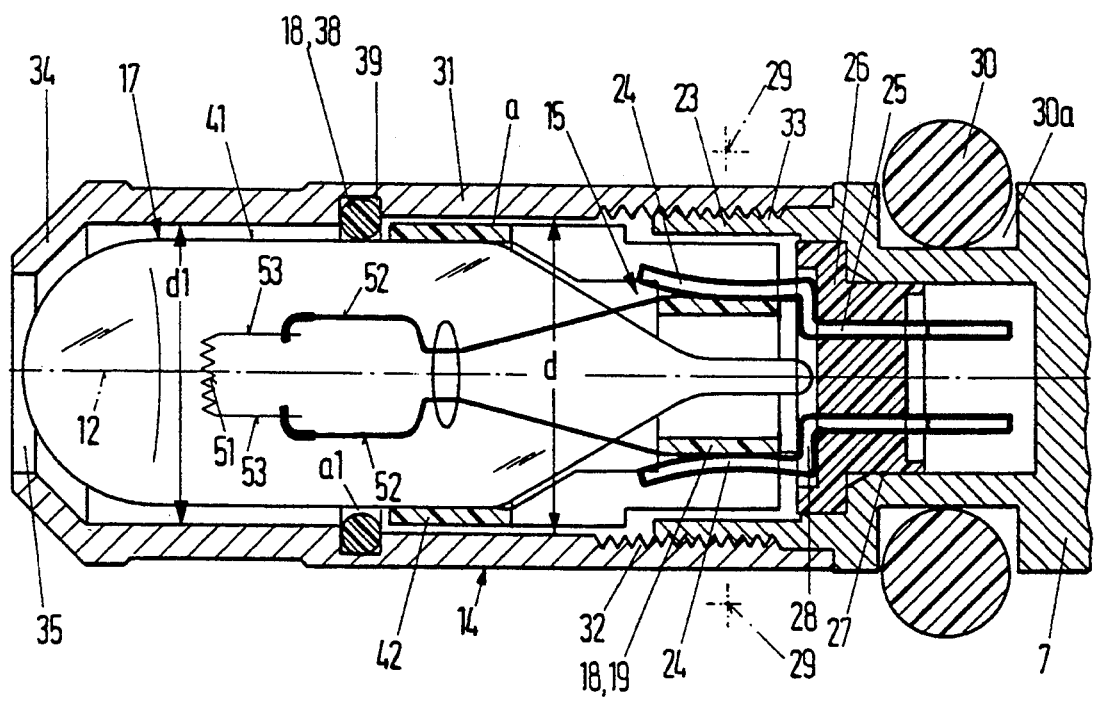
FIG. 3 shows, in an enlarged longitudinal section, the lamp holder wherein the lamp holder is rotated through 90° about the longitudinal centre axis relative to the arrangement shown in FIG. 2.

The front instrument part 1 is a drilling handpiece 2, which has, as is conventional, a gripping sleeve 3 with a tool head 4 at its front end from which an exchangeable drilling tool 5 projects laterally or downwardly. The gripping sleeve 3 has at its rear end a coaxial coupling recess 6 into which the coupling pin 7 can be inserted and can be locked detachably by known locking means 8. The coupling pin 7 is part of a coupling body 9 that is accommodated in the rear instrument part 11. The coupling recess 6 or coupling bush and the coupling pin 7 are circular in cross-section so that the front instrument part 1 can rotate freely about the longitudinal centre axis 12 of the instrument when in its mounted position.

Extending through the quick-fit coupling, indicated generally by 13, are a plurality of medium lines which first extend axially in the coupling pin 7, pass radially and sealingly through its outer surface and the inner surface of the coupling recess 6, and then extend further axially in the handpiece 2.

The lamp holder 14 is arranged at the front end of the coupling pin 7. It includes a plug-in socket 15 and a radially effective damping element 16 for the lamp 17 that has a plug-in foot 18 with axis-parallel lateral faces 19 and a glass bulb 21, which in the present embodiment is elongated or cylindrical, extending forwards from the plug 18.

The plug-in socket 15 includes a plug-in bush 22, which is surrounded by a hollow cylindrical bush wall 23, and two leaf spring arms 24, spaced apart and arranged opposite one another relative to the longitudinal centre axis 12, which spring arms are each angled in a Z-shape and with their rear base section 25 engage in a base part 26 and are secured therein, e.g. by a press-fit. The base part 26, that preferably consists of insulating material such as plastics material, is a plug-shaped body having a flange at its front end and is press-fitted into a stepped bore 27 arranged coaxially with the plug-in socket 22 in the front end region of the coupling pin 7. The leaf spring arms 24 are offset radially outwards relative to the base sections 25, and the transverse sections 28 provided by the Z-shape bear with their rear sides against the front face of the base part 26 or are at a small distance therefrom. The leaf spring arms 24 are—viewed from the longitudinal centre axis 12—s- lightly bent around two axes of curvature 29 with their front ends bent outwards, the axes of curvature 29 extending transverse to the longitudinal centre axis 12 and parallel to one another.

There is a free space 20 between the bush wall 23 and the leaf spring arms 24. Recesses 20a are preferably provided in the bush wall 23 opposite the leaf spring arms 24 into which the leaf spring arms 24 can enter when bent outwards.

The lamp 17 is surrounded at a distance a by a sleeve-like or cap-like protective casing 31 which has an internal winding 32 in its inner end with which it is screwed onto an external thread 33 in the bush wall 23. Located coaxially in the cap bottom 34 is a hole 35 through which the light from the lamp 17 radiates forwards and is guided through a light conductor 36 to a lateral light outlet 37 aimed at the treatment area and arranged in the head region of the handpiece 2 on the tool side.

The lamp 17 held in the lamp holder 14 is, in the region of its plug-in foot 18, radially resiliently or floatingly held, elastically resiliently transverse to the axes of curvature 29, due to the spring force of the leaf spring arms 24, and is held so that it can move along the axes of curvature 29 between the leaf spring arms 24.

In the region of the glass bulb 21, the lamp 17 is supported radially elastically resiliently on all sides and thus springily. As shown in FIG. 3, this purpose is served by a ring 38 which sits in an inner circumferential groove 39 in the protective casing 31. The ring 38 may consist of hard elastic or of soft elastic material, in particular rubber or plastics material, and may bear with its inside against the outer surface area 41 of the glass bulb 21 or surround it at a small distance a1. In the present exemplary embodiment the supporting ring 38 is located in the middle longitudinal region of the glass bulb 21.

In the present exemplary embodiment the lamp 17 has radially protruding projections or a circumferential ring 42 in the rear peripheral region. It is advantageous to arrange the supporting ring 38 directly forward of the circumferential ring 42, whereby axial securement of the lamp 17 is provided because the supporting ring 38 provides a movement restriction for the circumferential ring 42. Depending on the size of the supporting ring 38 it can be advantageous for the internal diameter d behind the supporting ring 38 to be slightly larger than the internal diameter d1 forward of the supporting ring 38.

An O-sealing ring arranged in a peripheral groove 30a in the coupling pin 7 is indicated by 30.

Figure 4:
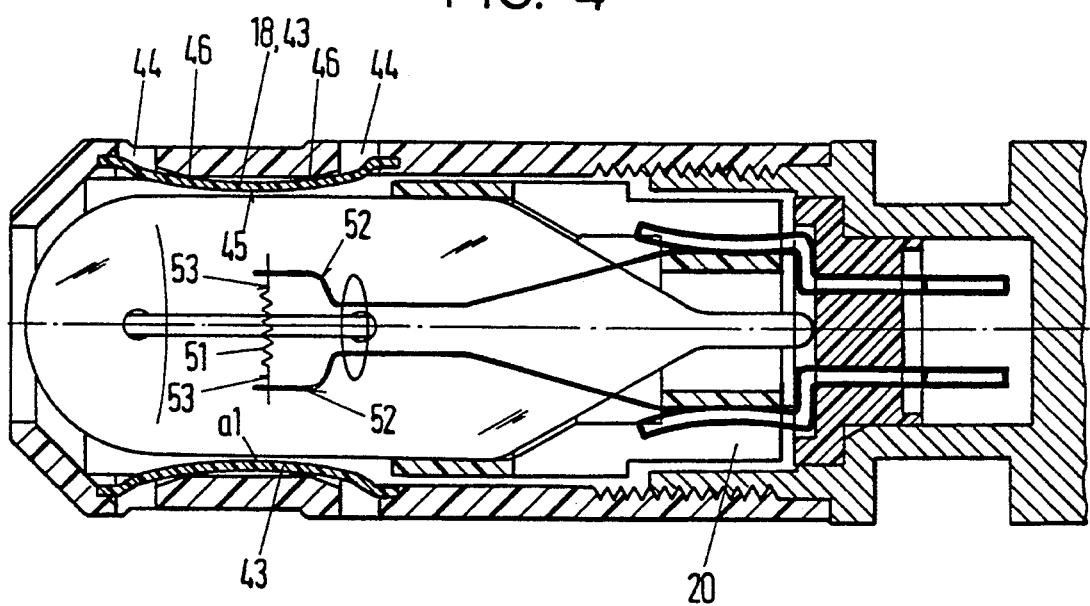
FIGS. 4 to 6 show, in longitudinal section, modified embodiments of the lamp holder.

In the embodiment shown in FIG. 4 instead of a supporting ring 38, a plurality, preferably three, spring elements 43 uniformly distributed around the periphery are provided which are held on the protective casing 31. In the present embodiment the spring elements 43 are formed by arc-shaped bands or strips extending in the longitudinal direction, the free ends of which sit in fastening holes 44 that are open at least on the inside and undercut. The preferably inwardly convex arc-shaped strips can be supported on the outside by the protective casing 31 forward of and behind the middle arc region 45 (see contact point 46). The end sections of the strips can be so offset that they extend in one and the same plane.

The arrangement is such that in their normal position the spring elements 43 are at a small distance a1 from the glass bulb 21 or bear against it. The, in particular, resilient supporting function of the spring elements 43 arises because they consist of either elastic material, in particular plastics material or rubber, or can bend radially outwards elastically. This provided to a certain extent a free swinging mount or an elastically resilient support for the glass bulb 21 wherein a small free space is provided due to the distance a1.

In the embodiments described above the body forming the plug-in socket 15, namely the front end region of the coupling pin 7, consists of metal such as, for example, steel and the protective casing may consist of a hard or non-resilient material such as plastics material or metal.

Figure 5:
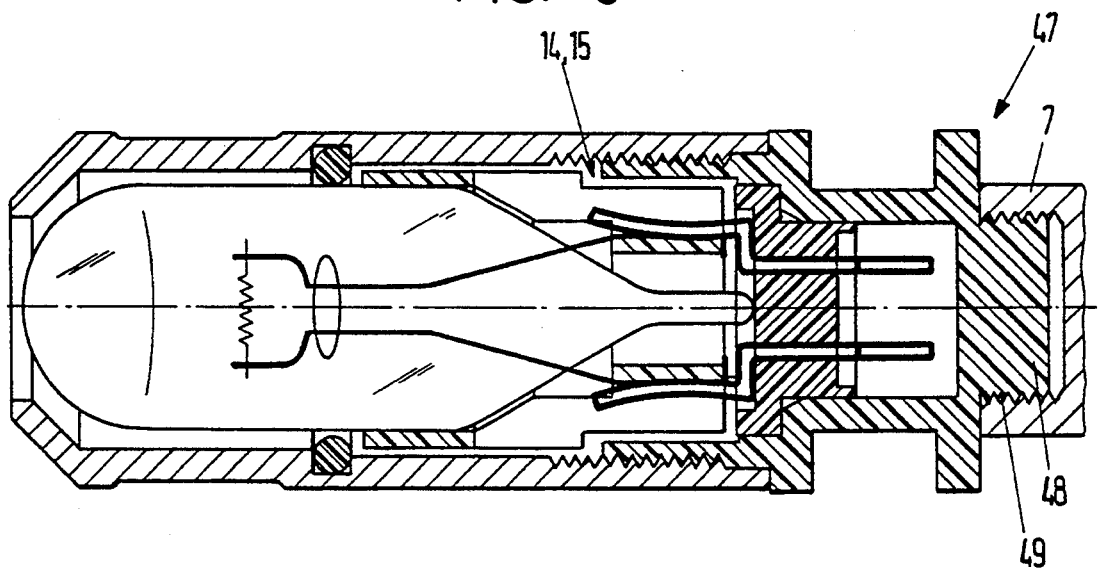

In distinction to the embodiment shown in FIG. 3, in the embodiment shown in FIG. 5 the part including the plug-in socket 15 is provided with an additional component 47 of elastic resilient material, such as plastics material or rubber, that is preferably mounted detachably, preferably screwed, to the front end of the coupling pin 7. This purpose can be served by a screw pin 48 with internal- or preferably external threads 49 that is screwed into corresponding threads on the coupling pin 7, preferably in a bush-shaped, forward recess therein.

The configuration of the component 47 corresponds otherwise to the front end region of the coupling pin 7 with the plug-in socket 15 as described above. The damping elements 16 described above may be provided in addition.

The component 47 represents a elastically resilient mount for the plug-in socket 15, that is effective, in particular, radially and if necessary also axially. Owing to this configuration the lamp holder 14 with the plug-in socket 15 can swing radially freely relative to the coupling pin 7, and owing to the elasticity of the component 47 will always be guided into the middle position. It is hereby possible for the protective casing 31 to be of hard or of elastic, resilient material.

Figure 6:
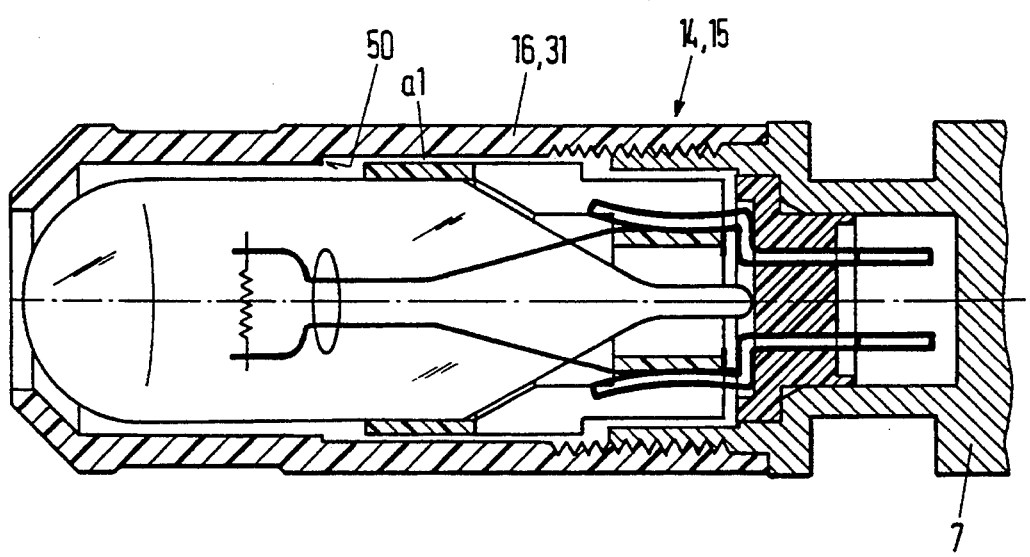

An embodiment of this kind is shown in FIG. 6. In this way the protective casing 31 forms the radial damping element 16 itself so that separate, elastic resilient damping elements are not needed. In this embodiment a small radial distance is provided between the inner surface area of the protective casing 31 and the periphery of the glass bulb 21 or its circumferential ring 42, or the inner surface area of the protective casing 31 may also bear against the circumferential ring 42 or the glass bulb 21. In this embodiment the body holding the plug-in socket 15 may likewise consist of elastic, resilient or preferably hard material and can be formed by the coupling pin 7.

Provided forward of the glass bulb 21 on the inner surface area of the protective casing 31 is a shoulder 50 facing the glass bulb which prevents the lamp 17 from moving out of the plug-in socket 15 in a form-fitting manner in the manner of a stop.

In the embodiments described above the lamp 17 is an electric incandescent lamp with a resistance wire, preferably in the form of a coil 51 extending diagonally, that is held by two support wires 52 in the glass bulb 21 and is connected to contact elements arranged on the lateral sides 19 that are in contact with the leaf spring arms 24. Electricity is supplied by connecting the base section 25, that preferably projects from the rear side from the base part 26, to an electric circuit (not shown).

In the embodiment shown in FIG. 3 the coil 51 is connected by holding wires 53 projecting at right angles from its ends to the free ends of the support wires 52 that are arranged in the same longitudinal centre plane, spaced on either side of the longitudinal centre axis 12, in the manner of a fork.

The arrangement of the coil 51 shown in FIGS. 4 to 6 is particularly advantageous. In this configuration the holding wires 53 extend in the longitudinal direction of or coaxially with the coil 51 and in a straight line to the free ends of the support wires 52. Hanging the coil 51 in this way contributes to avoiding failure of lamp 17. This is because the coil 51 is not sensitive with regard to radial oscillations because it does not have holding wires 53 extending along the longitudinal centre axis 12 with which, if present, the coil 51 would tend to oscillate radially and therefore be in greater danger of breaking.

The lamp holder 14 according to the invention can be used in all medical and in particular dental instruments in which vibrations occur. As a rule vibrations are caused by a motor drive for the treatment tool. In the dental field, apart from being used with motor- or turbine-driven handpieces or instruments, they can also be used with so-called tooth scaling devices or other instruments. Usage is not restricted to arranging the lamp 17 centrally in the instrument as is the case in the present exemplary embodiment. The lamp may also be arranged eccentrically which is in particular necessary with instruments in which the treatment tool is driven by drive train. In the case of two-part instruments the lamp holder 14 can be used either in the front or in the rear instrument part.

What is claimed is:

1. In a medical or dental instrument comprising a base and driven treatment tool and a lamp mounted on the base, said lamp being arranged to supply illumination to the region surrounding the treatment tool, and a lamp holding arrangement comprising a pair of spring elements also mounted on the base and biased toward one another to press against a plug-in foot of the lamp and to allow the lamp to swing freely and a dampening arrangement comprising a dampening element mounted between said lamp and said base.

2. An instrument according to claim 1, wherein said spring elements are leaf spring arms which extend parallel to each other.

3. An instrument according to claim 1, wherein the dampening element is arranged between a holder for the lamp and said base.

4. An instrument according to claim 1, wherein the dampening element is arranged between the lamp and a holder for the lamp.

5. An instrument according to claim 4, wherein the holder has a protective casing accommodating the lamp that can be connected to a base part providing a plug-in socket.

6. An instrument according to claim 5, wherein the protective casing itself consists of elastic material and forms the damping element.

7. An instrument according to claim 3 or 4, wherein the damping element 15 at a small redial distance from the lamp.

8. An instrument according to claim 3 or 4, wherein the damping element consists of flexible elastic material.

9. An instrument according to claim 3 or 4, wherein the damping element is formed by an O-ring.

10. An instrument according to claim 3 or 4, wherein at least three damping elements are distributed around the periphery of and are each formed by a convex strip curved towards the lamp, ends of said strips being held on, the protective casing.

11. An instrument according to claim 1, 3 or 4, wherein the lamp has a diametrically extending resistance wire or a diametrically arranged coil which is connected by holding wires that extend diametrically further from its ends to support wires arranged in the form of a fork.

* * * * *